United States Patent [19]

Crump et al.

[11] Patent Number: 4,500,356
[45] Date of Patent: Feb. 19, 1985

[54] METHYLENEPHOSPHONIC ACID DERIVATIVES OF BIS(AMINOALKYL)PIPERAZINES AS CEMENT SET RETARDING AGENTS

[75] Inventors: Druce K. Crump, Lake Jackson; Jaime Simon, Angleton; David A. Wilson, Richwood, all of Tex.

[73] Assignee: The Dow Chemical Company, Midland, Mich.

[21] Appl. No.: 583,527

[22] Filed: Feb. 24, 1984

[51] Int. Cl.$^3$ .............................................. C04B 7/35
[52] U.S. Cl. ...................................... 106/90; 106/315
[58] Field of Search .................................. 106/90, 315

[56] References Cited

U.S. PATENT DOCUMENTS

| | | | |
|---|---|---|---|
| 3,409,080 | 11/1968 | Harrison | 166/31 |
| 3,794,506 | 2/1974 | Schmidt et al. | 106/90 |
| 3,865,803 | 2/1975 | Falkehag | 260/124 A |
| 3,964,921 | 6/1976 | Persinski et al. | 106/90 |
| 4,040,854 | 8/1977 | Persinski et al. | 106/90 |
| 4,066,469 | 1/1978 | Shiel et al. | 106/89 |
| 4,225,361 | 9/1980 | Joseph | 106/111 |
| 4,401,473 | 8/1983 | Kleiner et al. | 106/109 |

OTHER PUBLICATIONS

Chem. Abstracts: 97, 112352a—"Plugging Composition for Cementing Oil and Gas Wells", Dytyuk, L. T. et al.
Chem. Abstracts: 97, 26178a—"Plugging Fluids for Cementing Deep Petroleum and Gas Wells", Alekseev, P. D., et al.
Chem Abstracts: 98, 58912p—"Improvement of Casing Cementation in Deep and Ultradeep Wells, Part 2. Deep Well Cements and Additives," Arens, K. H. et al.
SU-640-019, "Plugging Mixture for High-Temperature Oil or Gas Wells—Comprises Portland Cement and 1-Hydroxye Ethylidene-Phosphonic Acid Sodium or Potassium Salt", Khariv I YU.
"Additives Tailor Cement to Individual Wells", P. N. Parker, C. Clement, *The Oil and Gas Journal*, Mar. 14, 1977, vol. 75.

*Primary Examiner*—James Poer
*Attorney, Agent, or Firm*—A. C. Ancona

[57] ABSTRACT

Methylenephosphonic acid derivatives of bis(aminoalkyl)piperazine are employed as cement set retarding additives. The compounds must have at least one of the amine hydrogens phosphonomethylated.

16 Claims, No Drawings

METHYLENEPHOSPHONIC ACID DERIVATIVES OF BIS(AMINOALKYL)PIPERAZINES AS CEMENT SET RETARDING AGENTS

BACKGROUND OF THE INVENTION

The invention pertains to aqueous hydraulic cement slurry compositions containing particular set retarders which are phosphonic acid derivatives of adducts of bis(aminoalkyl)piperazines.

Hydrophobic-substituted phosphonic or phosphinic acids and their alkali metal salts have been used in cements, primarily soil/cement mixtures, to improve the freeze-thaw properties and salt-resistance. Six- to eighteen-carbon alkyl phosphonic acids or their alkali metal salts are so described in U.S. Pat. No. 3,794,506. A plugging mixture for high temperature oil and gas wells comprising Portland cement and 1-hydroxy ethylidenephosphonic acid trisodium or tripotassium salts as set time extenders is described in Derwent abstract 71376B/39 (1979) of USSR Pat. No. 640,019. The use of these phosphonate salts at temperatures of 75° to 150° C. in amounts of 0.1-0.3% by weight is described in the abstract.

Other organic phosphorous acid derivatives are taught to be useful additives in cement compositions as turbulence-inducing and flow-property improver additives (U.S. Pat. Nos. 3,964,921 and 4,040,854, respectively). Another turbulence-inducer is a pyrolysis product of urea and a bis(alkylenepyrophosphate) (U.S. Pat. No. 3,409,080).

Alkylene diphosphonic acids and their water soluble salts are described as set time extenders and water reducing agents for gypsum plasters (U.S. Pat. No. 4,225,361). Lignins which have been phosphonoalkylated through an ether linkage or corresponding sulfonates, sulfides, hydroxyl or amine derivatives are taught to be useful primarily as dispersants or surfactants (U.S. Pat. No. 3,865,803) and are also said to be useful as "cement additives" without indicating specific uses.

Ultra-rapid hardening Portland cement compositions are described which contain various acid salt additives (U.S. Pat. No. 4,066,469). It states that use of acid phosphates as the acid salt additives is excluded since the phosphates have a characteristically powerful retarding property peculiar to them.

Most of the cement used in oil wells is called portland cement. Portland cement is manufactured by calcining raw materials consisting of limestone, clay, shale, and slag together at 2,600° to 2,800° F. in a rotary kiln.

The resulting material, is cooled and interground with small percentages of gypsum to form portland cement. In addition to the above raw materials, other components such as sand, bauxite, iron oxide, etc., may be added to adjust the chemical composition depending upon the type of portland cement desired.

The principal components of the finished portland cement are lime, silica, alumina, and iron. These components form the following complex compounds: Tricalcium aluminate, ($3CaO.Al_2O_3$), tetracalcium aluminoferrite, ($4CaO.Al_2O_3.Fe_2O_3$), tricalcium silicate, ($3CaO.SiO_2$), and dicalcium silicate, ($2CaO.SiO_2$).

When water is added to cement, setting and hardening reactions begin immediately. The chemical compounds in the cement undergo the processes of hydration and recrystallization which results in a set product. The maximum amount of water that can be used with an oil-well cement is the amount which can be added before solids separation occurs. The minimum amount of water is the amount required to make the slurry pumpable. Therefore, the normal water ratio is governed by the maximum and minimum limits for a particular class of cement.

Thickening time is the time that the cement remains pumpable in the well. This is the most critical property of an oil-well cement. The thickening time has to be long enough to be pumped into place and short enough to permit operations to resume quickly. Generally, 3 hours provides the necessary placement time plus a safety factor.

Other factors, such as fluid loss, viscosity and density must be taken into consideration and additives are known to the art-skilled which affect each of these factors as well as that of set, or thickening, time as mentioned above. Another parameter which has an effect on set time is temperature. Cement sets more rapidly as the temperature increases. This must be taken into consideration particularly when pumping cement into deeper wells since temperature increases as the depth of the well becomes greater. Temperature also affects the strength of the cement, the strength becoming less as the temperature increases.

Because of this temperature effect, it is important to retard the setting of the cement employed in the deeper wells.

It has now been discovered that certain new phosphonomethylated bis(aminoalkyl)piperazines are useful in aqueous cement slurries as set retarding additives. Some of these compounds are chelating agents, while others are useful as threshold agents in retarding the precipitation of metal ions from aqueous solution. However, all such compounds which are useful as cement set-retarders must contain at least one methylenephosphonate group.

SUMMARY OF THE INVENTION

The compounds useful as cement retarders in aqueous cement slurries are methylene phosphonic acid derivatives having the following formula:

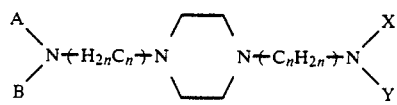

wherein n is 2-3 and wherein substituents A, B, X and Y each are independently selected from radicals including hydrogen; hydroxyalkyl (wherein the alkyl group contains 2-6 carbon atoms); methylenephosphonic, methylene-, ethylene- and propylenesulfonic; hydroxymethyl-, hydroxyethyl- and hydroxypropylsulfonic acid radicals; carboxylic acid radicals (having 2-4 carbon atoms) and the alkali, alkaline earth metal, ammonium and amine salts of any of the phosphonic, sulfonic or carboxylic acid derivatives. At least one of A, B, X and Y must be a methylenephosphonic acid radical or a salt thereof.

DETAILED DESCRIPTION OF THE INVENTION

The compounds useful in the process of the present invention have been disclosed in our cofiled and copending U.S. patent application entitled "Bis(aminoalkyl)Piperazine Derivatives and Their Use as Metal Ion Control Agents".

Representative of preparation of the compounds is the following example.

Preparation

Deionized water (10 g) and 20.0 g (0.10 mole) of bis(aminopropyl)piperazine were weighed into a 250-ml round-bottom reaction flask equipped with a water-cooled reflux condenser, mechanical stirrer, thermometer with a temperature controller, and an addition funnel. Approximately 40 g of concentrated HCl solution and 38.5 g (0.47 mole) of phosphorous acid were added to the aqueous amine solution and the reaction mixture heated to reflux and maintained for on hour. Aqueous 37% formaldehyde solution (34.0 g—0.42 mole) was added to the addition funnel and added over a one-hour period. The reaction mixture was heated at reflux for an additional four hours and then cooled.

The above compound and others were tested for retarding the setting of cement according to the following procedure:

Retarder Screening Procedure

1. The following ingredients were weighed:
   cement—100 g
   water—38 g
   additive—0.2 g active
2. Water and liquid additive were mixed.
3. Cement added to the liquid, bottle closed tightly and mixed by shaking.
4. Bottle placed in a preheated 180° F. (82° C.) bath.
5. Setting of cement checked after 6 and 24 hours.

A blank was always run without the additive for comparison. The compounds, identified by reference to the formula in the Summary above, and the results of the above test are shown in the Table.

The preparation of the products used in the above tests is detailed in our aforementioned copending application.

The compounds of the invention are particularly advantageous when used in cement slurries placed in oil wells wherein the temperature is 180° F. (82° C.) or above. Many of the known cement retarding additives are operable only at lower temperatures and frequently decompose at the higher temperatures at which the present additives work to retard the setting of cement.

organic phosphonate, the improvement which comprises employing a compound which is a phosphonomethylated bis(aminoalkyl)piperazine having the formula

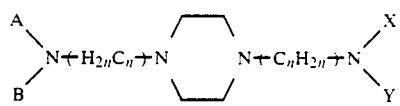

wherein n is 2-3 and wherein substituents A, B, X and Y each are independently selected from radicals consisting of hydrogen, hydroxyalkyl (wherein the alkyl group contains 2-6 carbon atoms); methylenephosphonic; methylene-, ethylene- and propylenesulfonic; hydroxymethyl-, hydroxyethyl- and hydroxypropylsulfonic acid radicals; carboxylic acid radicals (having 2-4 carbon atoms) and the alkali, alkaline earth metal, ammonium and amine salts of any of the phosphonic, sulfonic or carboxylic acid derivatives, and wherein at least one of A, B, X and Y is a methylenephosphonic acid radical or a salt thereof.

2. The process of claim 1 wherein the compound is one in which each A, B, X and Y is a methylenephosphonic acid group or a salt thereof.

3. The process of claim 1 wherein the compound employed is one in which three of A, B, X and Y substituents are methylenephosphonic acid groups and the remaining one is hydrogen.

4. The process of claim 3 wherein the compound employed contains a hydroxypropylsulfonic acid group in place of the remaining amine hydrogen.

5. The process of claim 3 wherein the acid groups of the compound employed are in the salt form.

6. The process of claim 4 wherein the acid groups of the compound employed are in the salt form.

7. The process of claim 3 wherein the compound employed contains a —CH$_2$COOH group in place of the amine hydrogen.

8. The process of claim 3 wherein the compound employed contains a hydroxypropyl group in place of the amine hydrogen.

9. The process of claim 7 wherein the acid groups are in the salt form.

10. The process of claim 8 wherein the acid groups are in the salt form.

TABLE

| | | Additive Compound | | | | Time | |
|---|---|---|---|---|---|---|---|
| Ex. | n | A | B | X | Y | 6 Hrs. | 24 Hrs. |
| 1 | 3 | —CH$_2$PO$_3$H$_2$ | —CH$_2$PO$_3$H$_2$ | —CH$_2$PO$_3$H$_2$ | —CH$_2$PO$_3$H$_2$ | retarding, not set | retarding, not set |
| 2 | 3 | " | " | " | H | retarding, not set | retarding, not set |
| 3* | 2 | " | " | " | —CH$_2$PO$_3$H$_2$ | retarding, not set | retarding, not set |
| 4* | 2 | " | " | " | H | retarding, not set | retarding, not set |
| 5* | 2 | " | " | " | —CH$_2$COOH | retarding, not set | retarding, not set |
| 6* | 2 | " | " | " | —CH$_2$CH(OH)—CH$_2$SO$_3$H | retarding, not set | retarding, not set |
| 7 | 3 | " | " | " | —CH$_2$CH(OH)—CH$_2$SO$_3$H | retarding, not set | retarding, not set |
| 8* | 2 | " | " | " | —CH$_2$CH(OH)CH$_3$ | retarding, not set | retarding, not set |
| 9* | 2 | —CH$_2$COOH | —CH$_2$COOH | —CH$_2$COOH | —CH$_2$COOH | set | set |
| Blank | | | —None— | | | set | set |

*neutralized with aqueous caustic solution

We claim:

1. In a process for retarding the setting of an aqueous cement slurry which comprises adding to said slurry an 11. The process of claim 5 wherein the salt is that of sodium.

12. The process of claim 6 wherein the salt is that of sodium.

13. The process of claim 9 wherein the salt is that of sodium.

14. The process of claim 10 wherein the salt is that of sodium.

15. The process of claim 1 wherein the temperature of the cement slurry is at least 180° F. (~82° C.).

16. The process of claim 1 wherein the cement slurry is injected into an oil well.

* * * * *